United States Patent [19]

Paulson

[11] Patent Number: 5,538,015
[45] Date of Patent: Jul. 23, 1996

[54] SHOULDER MOTION CONTROLLING HARNESS

[76] Inventor: John C. Paulson, 269 N. 600 East, American Fork, Utah 84003

[21] Appl. No.: 375,363

[22] Filed: Jan. 19, 1995

[51] Int. Cl.⁶ ..................................................... A61F 5/37
[52] U.S. Cl. ......................................... 128/869; 128/875
[58] Field of Search .................................. 128/846, 869, 128/874, 875, 876, 877, 878; 602/4, 5, 19, 20; 2/44, 45, 92

[56] References Cited

U.S. PATENT DOCUMENTS

| 686,338 | 11/1901 | Ready | 128/881 |
|---|---|---|---|
| 1,808,422 | 6/1931 | MacDonald | 602/4 |
| 4,446,858 | 5/1984 | Verter | 602/4 |
| 4,476,859 | 10/1984 | Kloepfer | 602/4 |
| 4,598,701 | 7/1986 | Schaefer | 602/19 |
| 4,598,703 | 7/1986 | Lindemann | 602/4 |
| 4,862,878 | 9/1989 | Davison | 2/44 |
| 5,018,513 | 5/1991 | Charles | 602/19 |
| 5,290,218 | 3/1994 | Kilbey | 128/869 |

Primary Examiner—Michael A. Brown
Attorney, Agent, or Firm—Delbert R. Phillips

[57] ABSTRACT

The Shoulder Motion Controlling Harness is a light weight strong porous and durable unit that can be comfortably worn for long periods of time which is fully adjustable and allows for severe to light restriction of arm and shoulder movement, enabling each athlete to enjoy an optimal level of protection, mobility, and comfort. It is composed of a chest anchor band with reinforcements that provide strength and shape. The chest anchor band is attached to a biceps cuff by a rotation controlling strap and an extension restriction strap. An over the shoulder strap provides vertical stability to the chest anchor band.

12 Claims, 3 Drawing Sheets

SHOULDER MOTION CONTROLLING HARNESS

BACKGROUND OF THE INVENTION

There have been many attempts to provide shoulder bracing to protect an active injured shoulder. Most however are bulky and very restrictive as illustrated in U.S. Pat. No. 5,163,450. U.S. Pat. No. 5,188,587 is similar to the claimed invention however it has no over the shoulder strap to control the vertical position of the chest band. The patented device has a cup that extends from the neck, over the shoulder to the upper portion of the biceps with two straps that are anchored to the chest to control rotation of the shoulder. The present Shoulder Motion Controlling Harness accomplishes the same object by eliminating the uncomfortable cup and one of the rotation straps thereby providing more comfort and freedom of movement to the wearer without sacrificing motion control of the shoulder..

The Shoulder Motion Controlling Harness is effective in avoiding subluxation of the shoulder by limiting abnormal hyper extension of the shoulder while permitting limited movement, sufficient to allow athletes to safely resume training and competition. The Harness described herein can be used by athletes desiring a prophylactic approach to injury, or by injured athletes desiring post-injury/surgery protection during rehabilitation. The Shoulder Motion Controlling Harness allows for a significant range of movement, thus enabling athletes to resume competition at near-normal performance levels with reduced probability of recurrence of initial injury. Athletes will compete with more confidence knowing that the risk of re injury is substantially reduced. Applications include, but are not limited to: Football, Hockey, Volleyball, Skiing, Motor-Cross Biking, and Rodeo.

The Shoulder Motion Controlling Harness is a light weight strong porous and durable unit that can be comfortably worn for long periods of time, which is fully adjustable and allows for severe to light restriction of arm and shoulder movement, enabling each athlete to enjoy an optimal level of protection, mobility, and comfort. The materials used in the construction are washable in cold water and should be air dried.

BRIEF DESCRIPTION OF INVENTION

The Shoulder Motion Controlling Harness is composed of 5 components which are (a) a chest anchor band having two ends that are fastened together forming a band having a front and back side when encircling the chest (b) a biceps cuff encircling the mid upper arm of the shoulder to be protected (c) a rotation controlling strap having two ends, the first end being attached to the biceps cuff over the lateral aspect of the upper arm and the second end being attached to the front portion of the chest anchor band towards the center of the chest by a fastening means located on the outside surface of the chest anchor band, when in place to position the rotation controlling strap, to restrict rotation of the humerus when attached to the biceps cuff (d) an over the shoulder strap positioned over the non-protected shoulder and fastened to the chest anchor band on the center of the front side and back side and (e) an extension restricting strap fastened between the biceps cuff and the chest anchor band at a point below the axilla of the shoulder to be protected. The chest anchor band is positioned immediately below pectoral muscles and has fastening means at the ends. The chest anchor band has stiffeners that provide strength, stability and shape. The biceps cuff is composed of one piece having stiffeners which provide shape and strength located at the two ends of the biceps cuff and in the center. The biceps cuff has closure means at each end allowing the cuff to encircle the mid upper arm below the shoulder when the two ends are closed.

DETAILED DESCRIPTION OF THE INVENTION

Figure 1:
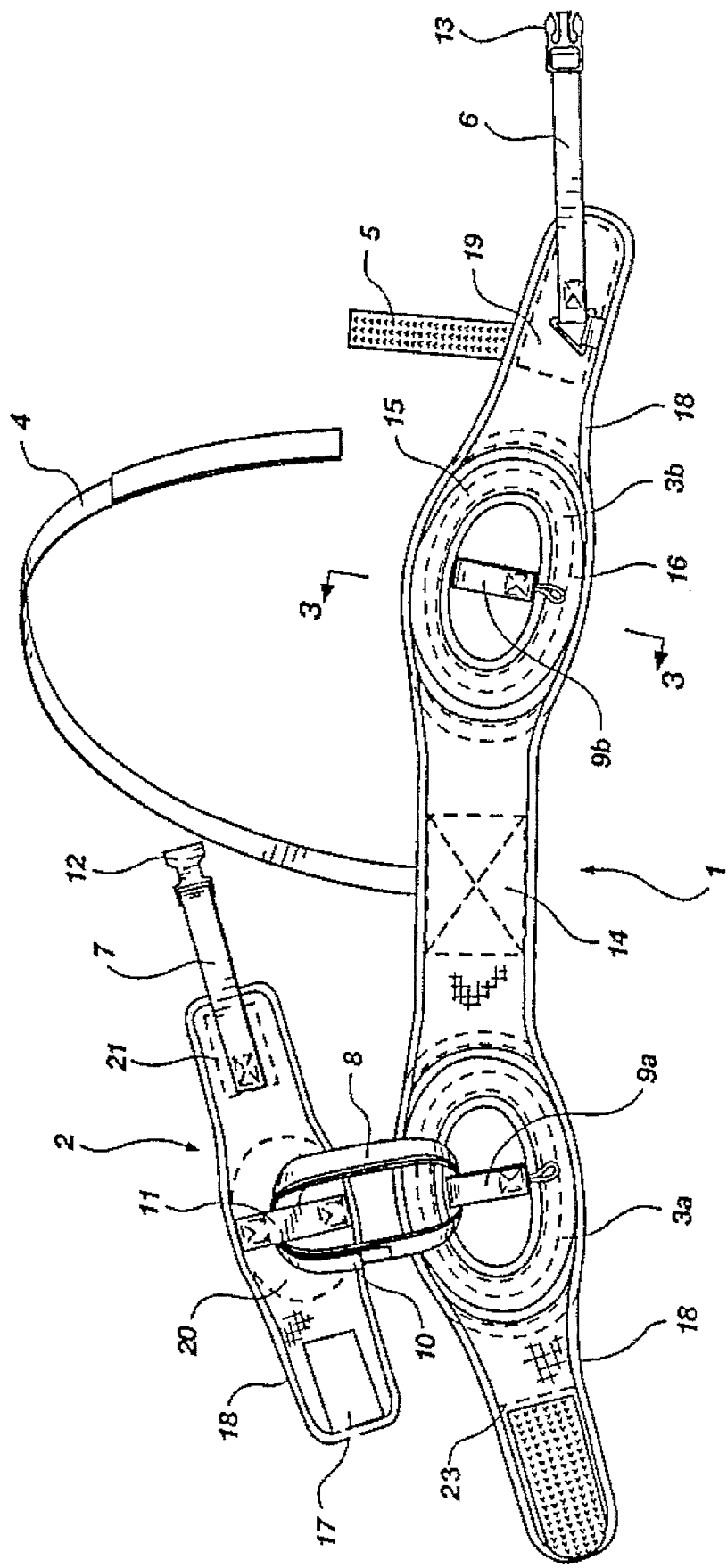
FIG. 1 is a view of the Shoulder Motion Controlling Harness fully extended to show all the components.
Figure 2:
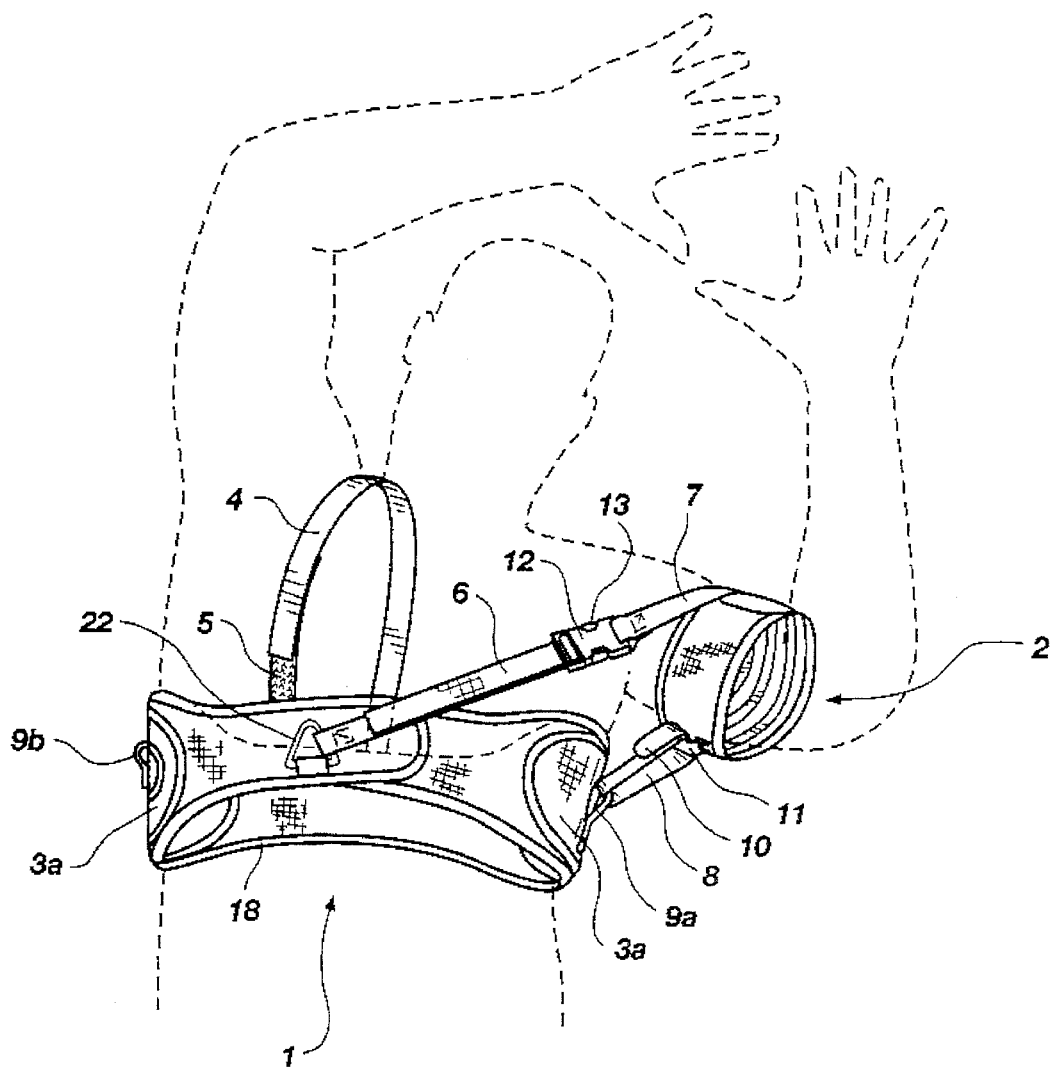
FIG. 2 shows the Shoulder Motion Controlling Harness in position wrapped around the chest and arm.
Figure 3:
FIG. 3 shows a cutaway view of a reinforced area of the chest anchor band showing the various layers of stiffening material that are inserted between the outside layers of nylon mesh.

When the chest anchor band (1) is in place around the chest, oval reinforcing pads and reinforced areas (3a) and (3b) are positioned on opposite sides of the chest beneath the axilla to provide rigidity, strength, stability and shape and to prevent the Shoulder Motion Controlling Harness (FIG. 1) from slipping while in use. A reinforced area (14) is located in the center of the back portion of the chest anchor band (1). The chest anchor band (1) has a reinforced area (19) at the first end which is over the center of the chest when the Shoulder Motion Controlling Harness is in place. The over the shoulder strap is composed of two sections (4) and (5). The first section (4) of the over the shoulder strap is attached to the chest anchor band (1) at the reinforced area (14). The second section (5) of the over the shoulder strap is fastened to the reinforced area (19). "VELCRO®" (hook and loop fastening device) fasteners are stitched to the ends of the first section (4) and second section (5) of the over the shoulder strap providing closure and adjustability in the length of the over the shoulder strap. These "VELCRO®" (hook and loop fastening device) closures allow the over the shoulder strap to accommodate various torso lengths. The position of the attachments of the over the shoulder strap to the chest anchor band (1) allows the Shoulder Motion Controlling Harness to be worn on the right or left shoulder and controls the vertical position of the chest anchor band (1) on the chest. The rotation controlling strap is composed of two pieces (6) and (7) connected by an adjustable fastening means (12) and (13) which allow the rotation controlling strap to be adjusted in length. The first piece (6) is connected through connector (13) to connector (12) on the second piece (7) of the rotation controlling strap. The first piece (6) is attached to the chest anchor band by a three sided ring (22). The second piece (7) is attached to the biceps cuff on the reinforced area (21). The reinforced areas (20),(21) and (17) in the biceps cuff provides shape and strength to the biceps cuff (2). "VELCRO®" (hook and loop fastening device) as an adjustable fastener is applied permanently over reinforced areas (17) and (21) to provide adjustability for the biceps cuff. The biceps cuff (2) optionally is lined with non slip material. The extension restricting strap (8) is a one piece strap having "VELCRO®" (hook and loop fastening device) fasteners (10) on each end. The extension restricting strap (8) is threaded through loop of material (11) attached to the biceps cuff (2) to the reinforced area (20) which is located over the medial aspect of the upper arm when the Shoulder Motion Controlling Harness is worn. The extension restricting strap(8) is also threaded through a loop of material (9a) or (9b) located over the center of the reinforced areas (3a) and (3b) of the chest anchor band. When the two ends of the extension restricting strap (8) are fastened together by a "VELCRO®" (hook and loop fastening device) strips attached to the ends of the extension restricting strap (8), a continuous band is formed that connects the biceps cuff by loop (11) to the chest anchor band (1) by loop (9a) or (9b) depending upon which shoulder is to be protected, and thereby controlling the angle of extension of the shoulder. The chest anchor band (1) has a "VELCRO®" (hook and loop fastening device) affixed over the reinforced ends (23) and (19) allowing adjustable closure of the chest anchor band (1) around the chest. A three sided ring (22) is located on the outside surface of the front side of the chest anchor band to anchor the first piece of the rotation controlling strap (6) to the chest anchor strap (1).

The biceps cuff (2) and the chest anchor band (1) are fabricated from two thicknesses of soft nylon mesh fabric with multiple layers of stiff and rigid nylon mesh reinforcements inserted at the areas requiring reinforcement (3a), (3b),(14),(20),(21),(23),(17) and (19). Optionally foam pads are glued and stitched on the inner surface of the reinforced areas (3a), and (3b) of the chest anchor band (1), and (20) of the biceps cuff (2). Strips of a non slip rubberized material are glued and sewed to the inner surface of these reinforced areas (3a), (3b), and (20) as lining next to the skin or clothing, preventing slippage when worn. The two thicknesses of soft nylon mesh, which are the outer and inner surfaces of chest anchor band (1) and biceps cuff (2), are bound together by binding (18).

Figure 4:
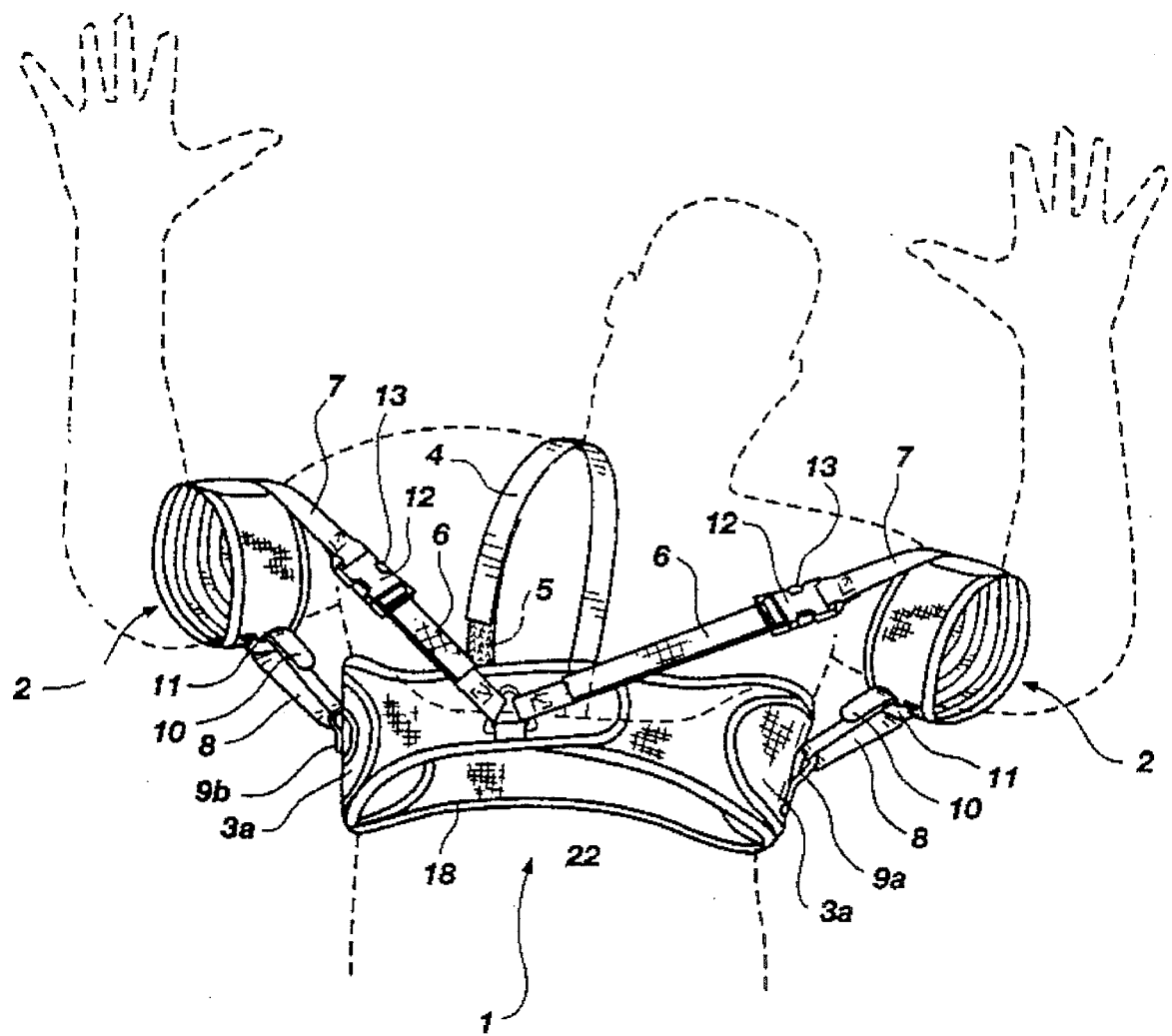
FIG. 4 shows a Shoulder Motion Controlling Harness with two biceps cuffs, two rotation controlling straps, and two extension restriction straps in position, wrapped around the chest and two arms.

Additionally a second biceps cuff may be attached to the chest anchor band to provide protection for both shoulders as depicted in FIG. 4. This second biceps cuff uses a second rotation controlling strap and a second extension controlling strap. In this configuration of the Shoulder Motion Controlling Harness, the over the shoulder strap may be worn over either shoulder.

The components of the Shoulder Motion Controlling Harness can be fabricated by the use of standard cloth fabrication techniques such as cutting, stitching, gluing and sewing.

The descriptions hereinabove are by way of illustration only and are not intended to limit the scope of the invention as set forth in the claims below.

What is claimed is:

1. A shoulder motion controlling harness comprising;

a chest anchor band having two ends;

said ends fastened together forming a band;

said band having a front side and back side when encircling the chest; said chest anchor band being positioned immediately below the pectoral muscles when in place on said chest;

a biceps cuff encircling the upper arm of the shoulder to be protected;

a rotation controlling strap having a first end and a second end;

said first end of said rotation controlling strap being attached to said biceps cuff over the lateral aspect of said upper arm;

said second end of said rotation controlling strap having a first attachment located on the front central portion of said chest anchor band;

an over the shoulder strap positioned over the non protected shoulder having a first end and a second end;

said first end of said over the shoulder strap being fastened to said chest anchor band on the center of said front side;

said second end of said over the shoulder strap being attached to said back side of said chest anchor band;

an extension restricting strap connecting said biceps cuff and said chest anchor band; and said extension restricting strap being positioned to connect said biceps cuff at a point over the inner aspect of said upper arm and said chest anchor band at a point below the axilla of the shoulder to be protected.

2. A shoulder motion controlling harness as defined in claim 1, wherein said chest anchor band has hook and loop fastening devices on said ends.

3. A shoulder motion controlling harness as defined in claim 1, wherein said over the shoulder strap is composed of a first and second section secured by an adjustable fastening means.

4. A shoulder motion controlling harness as defined in claim 3, wherein said adjustable fastening means is hook and loop fastening device.

5. A shoulder motion controlling harness as defined in claim 3, wherein said first section of said over the shoulder strap is anchored to the center of said back side of said chest anchor band.

6. A shoulder motion controlling harness as defined in claim 3, wherein said second section of said over the shoulder strap is anchored to the center of said front side of said chest anchor band.

7. A shoulder motion controlling harness as defined in claim 1, wherein said chest anchor band contains a first and second shaping and reinforcing means located beneath the two axilla when said shoulder motion controlling harness is in place.

8. A shoulder motion controlling harness as defined in claim 7, wherein said shaping and reinforcing means are formed from multiple layers of stiff nylon mesh.

9. A shoulder motion controlling harness as defined in claim 7, wherein said chest anchor band has loops of material fastened over said first and said second shaping and reinforcing means.

10. A shoulder motion controlling harness as defined in claim 1, wherein said extension restricting strap comprises a strip of material with adjustable fastening means located on both ends;

said strip of material forming a continuous loop when said ends are fastened together;

said continuous loop of material connecting a second loop attached on the medial side of said biceps cuff with a third loop of material attached on the said chest anchor band under the axilla.

11. A shoulder motion controlling harness as claimed in claim 1 having a second biceps cuff, a second rotation controlling strap, and a second extension controlling strap.

12. A shoulder motion controlling harness comprising;

a chest anchor band having two ends;

said ends fastened together forming a band;

said band having a front side and back side when encircling the chest; said chest anchor band being positioned immediately below the pectoral muscles when in place on said chest;

a biceps cuff encircling the upper arm of the shoulder to be protected;

a rotation controlling strap having a first end and a second end;

said first end of said rotation controlling strap being attached to said biceps cuff over the lateral aspect of said upper arm;

said second end of said rotation controlling strap having a first attachment located on the front central portion of said chest anchor band;

an over the shoulder strap positioned over the non protected shoulder having a first end and a second end;

said first end of said over the shoulder strap being fastened to said chest anchor band on the center of said front side;

said second end of said over the shoulder strap being attached to said back side of said chest anchor band;

an extension restricting strap connecting said biceps cuff and said chest anchor band; and said extension restricting strap being positioned to connect said biceps cuff at a point over the inner aspect of said upper arm and said chest anchor band at a point below the axilla of the shoulder to be protected;

said extension restricting strap comprising;
 a strip of material with adjustable fastening means located on both ends;
 said strip of material forming a continuous loop when said ends are fastened together;
 said continuous loop of material connecting a second loop attached on the medial side of said biceps cuff with a third loop of material attached on the said chest anchor band under the axilla.

* * * * *